(12) United States Patent
Yagyu et al.

(10) Patent No.: US 10,863,752 B2
(45) Date of Patent: Dec. 15, 2020

(54) PLASMA STERILIZATION DEVICE

(71) Applicants: NATIONAL INSTITUTE OF TECHNOLOGY, Tokyo (JP); SAGA UNIVERSITY, Saga (JP); UNIVERSITY OF THE RYUKYUS, Okinawa (JP)

(72) Inventors: Yoshihito Yagyu, Nagasaki (JP); Tatsuya Misawa, Saga (JP); Akikazu Sakudo, Okinawa (JP)

(73) Assignees: National Institute of Technology, Tokyo (JP); Saga University, Saga (JP); University of the Ryukyus, Okinawa (JP)

( * ) Notice: Subject to any disclaimer, the term of this patent is extended or adjusted under 35 U.S.C. 154(b) by 273 days.

(21) Appl. No.: 15/771,169

(22) PCT Filed: Oct. 27, 2016

(86) PCT No.: PCT/JP2016/081799
§ 371 (c)(1),
(2) Date: Apr. 26, 2018

(87) PCT Pub. No.: WO2017/073641
PCT Pub. Date: May 4, 2017

(65) Prior Publication Data
US 2018/0317508 A1    Nov. 8, 2018

(30) Foreign Application Priority Data

Oct. 29, 2015 (JP) .................................. 2015-212715

(51) Int. Cl.
*A23B 7/015* (2006.01)
*A23L 3/26* (2006.01)
(Continued)

(52) U.S. Cl.
CPC ................ *A23B 7/015* (2013.01); *A23L 3/26* (2013.01); *A23L 3/266* (2013.01); *A23L 3/32* (2013.01);
(Continued)

(58) Field of Classification Search
CPC . A23B 7/015; A23L 3/26; A23L 3/266; A23L 3/32; H05H 2001/2418; H05H 2245/1225; H01T 19/00; H01T 19/04
See application file for complete search history.

(56) References Cited

U.S. PATENT DOCUMENTS 2,132,708 A    10/1938  Smith
4,467,200 A *   8/1984  Kalwar .................. H01T 19/00
                                                  250/324

(Continued)

FOREIGN PATENT DOCUMENTS

EP    2 175 693 A1    4/2010
EP    2 913 376 A1    9/2013
(Continued)

OTHER PUBLICATIONS

Translation of JP-2000295980-A (Year: 2000).*
(Continued)

*Primary Examiner* — Matthew P Travers
(74) *Attorney, Agent, or Firm* — Fay Sharpe LLP; James E. Scarbrough

(57) ABSTRACT

A plasma sterilization apparatus includes a voltage-applying unit that applies a voltage to a sterilization target having conductivity; a pair of electrodes that apply, in a discharged state, the voltage applied by the voltage-applying unit to the sterilization target via a dielectric; and a position changing unit that changes a relative position between the pair of electrodes and the sterilization target.

7 Claims, 13 Drawing Sheets

(51) Int. Cl.
  *A23L 3/32* (2006.01)
  *A61L 2/14* (2006.01)
  *H05H 1/24* (2006.01)
  *H01T 19/00* (2006.01)
  *A61L 2/24* (2006.01)

(52) U.S. Cl.
  CPC .................................... *A61L 2/14* (2013.01); *A61L 2/24* (2013.01); *H01T 19/00* (2013.01); *H05H 1/2406* (2013.01); *A23V 2002/00* (2013.01); *H05H 2001/2418* (2013.01); *H05H 2245/1225* (2013.01)

(56) References Cited

U.S. PATENT DOCUMENTS

| | | | | |
|---|---|---|---|---|
| 4,772,788 | A | * | 9/1988 | Tsutsui ............... B29C 59/103 250/324 |
| 5,038,036 | A | * | 8/1991 | Kouguchi ............ B29C 59/103 204/164 |
| 5,194,291 | A | * | 3/1993 | D'Aoust ............... C23C 16/505 118/723 R |
| 5,413,769 | A | * | 5/1995 | Okazaki ............... B01J 19/088 422/186 |
| 2018/0148209 | A1 | | 5/2018 | Watts et al. |

FOREIGN PATENT DOCUMENTS

| | | |
|---|---|---|
| EP | 2 913 378 A1 | 9/2013 |
| EP | 3 369 436 B1 | 10/2016 |
| JP | H07-296993 | 11/1995 |
| JP | H09-104985 | 4/1997 |
| JP | 11-137185 | 5/1999 |
| JP | 2000-295980 | 10/2000 |
| JP | 2000295980 A * | 10/2000 |
| JP | 2002-028441 | 1/2002 |
| JP | 2003-019785 | 1/2003 |
| JP | 2003-038933 | 2/2003 |
| JP | 3547413 | 2/2003 |
| JP | 2003-166062 | 6/2003 |
| JP | 2008-237047 | 10/2008 |
| JP | 2008-245784 | 10/2008 |
| JP | 2008-283909 | 11/2008 |
| JP | 2010-187648 | 2/2009 |
| JP | 2011-225954 | 11/2011 |
| JP | 2013-172657 | 9/2013 |
| JP | 2015-136605 | 7/2015 |
| WO | WO2017-073641 | 5/2017 |

OTHER PUBLICATIONS

Extended European Search Report for EP 16 85 9870, Munich, Date of Completiono f the Search Jun. 18, 2019, 32 Pages.
EPO Examination Report, 6 Pages, dated May 28, 2020, Application No. 16 870 470.8-1105, Dyden Corporation.
Extended European Search Report, Application No./U.S. Pat. No. 16870470.8-1105 / 3385356 PCT/JP2016084279, 8 pages, Apr. 16, 2019, The Hague.
Korea Office Action No. KR 10-2018-7009612, 5 Pages, dated Jul. 17, 2019.
Office Action in China No. CN 201680061089.X, 7 pages, no translation. Apr. 21, 2020.
Pergamon; Ultraviolet and Visable Luminescence Properties; 3 pages; www.elsevier.com/locate/radmeas. 2002.
Elsevier; ScienceDirect; Luminescence of La; Zorenko; Published 2007.
Elsevier; ScienceDirect; Novel UV-emitting single crystalline film; Zorenko; Published 2009.
JP 2015-233671 Decision to Grant and translation. Apr. 2017.
JP 2015-233671 Office Action and translation. Jan. 2017.

* cited by examiner

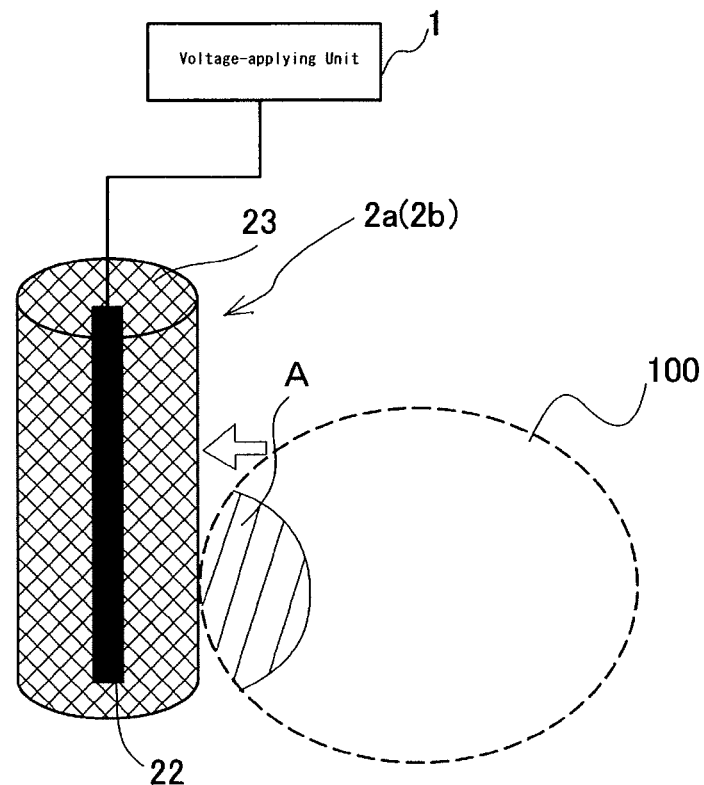
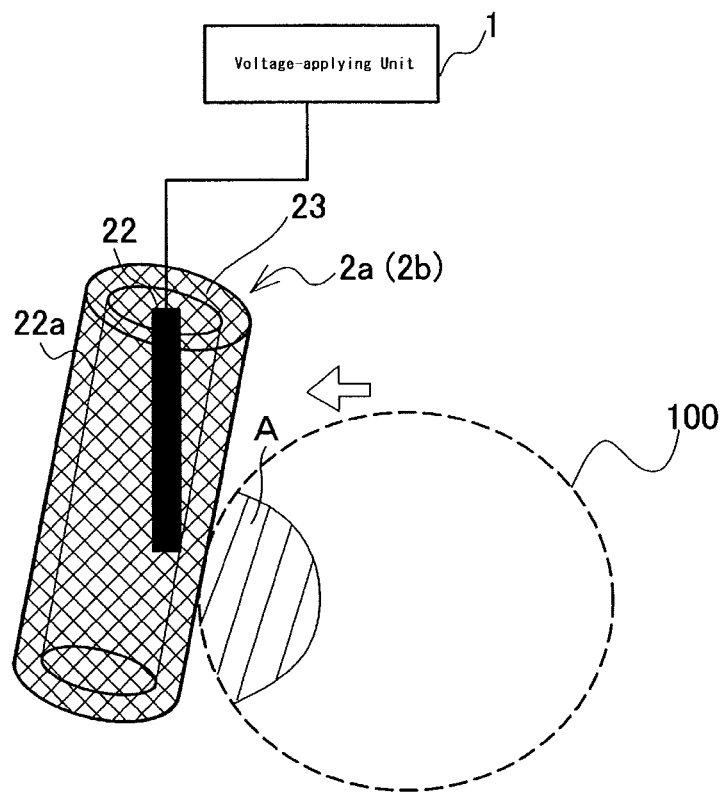

Cylindrical Shape

Plate Shape

Asteroid Shape in cross section

Concavo-convex Shape

Width of Sheet-shaped Electrode: 3mm

Width of Sheet-shaped Electrode: 5mm

PLASMA STERILIZATION DEVICE

TECHNICAL FIELD

The present invention relates to a plasma sterilization apparatus that sterilizes a sterilization target, utilizing discharged plasma, and specifically to a plasma sterilization apparatus that uniformly sterilizes a surface of a sterilization target having various kind of a three-dimensional shape.

BACKGROUND OF THE INVENTION

Plasma sterilization for sterilizing a target utilizing plasma is versatile, and its application field continues to expand. A field showing promise for the application field may include sterilization of agricultural products in the field of agriculture.

In the field of agriculture, currently, there is a global tendency for relaxing export and import restrictions for agricultural products, and it can be expected that such a tendency will intensify long distance transport of the agricultural produces.

Agricultural products contain various fungi clinging to their outer surfaces. However, they are characterized by difficulty in uniform sterilization through a rough sterilization, due to the fact that they have a wide variety of three-dimensional shapes. For sterilization of agricultural products, medical agents such as pesticides have conventionally been used for the purpose of inhibiting decomposition of agricultural products after harvesting. However, treatment of agricultural products for edible use with pesticides such as disinfecting agent or fungicide (a postharvest treatment) and residual pesticides concentrations may have strictly been regulated by their own laws and regulations of countries, thus leading to a situation of technical difficulty in long distance transport under existing conditions. Accordingly, there has been a demand for sterilization of agricultural products with a minimum of damage or adverse effects which are given to the agricultural products through sterilization.

It is expected that use of a plasma sterilization apparatus for sterilization of such agricultural products makes it possible to provide its high sterilization capacity so as to sterilize safely and adequately the agricultural products, especially without requiring medical agents or pesticides, which are harmful to a human.

There is known, as such a conventional plasma sterilization apparatus, for example, an apparatus in which a plasma irradiation step for irradiating an air plasma to a sterilization target to sterilize the sterilization target (see Patent Document No. 1). There is also known, for example, an apparatus in which a plasma sterilization apparatus that irradiates a radical as plasma-produced by a plasma unit, is provided within a conveyance passage between a fruit or vegetable-sorting step and a boxing step for fruits or vegetables conveyed via a transfer conveyer, to sterilize microorganisms clinging to surfaces of the fruits or vegetables, which have been conveyed by the above-mentioned transfer conveyer, by the above-mentioned sterilization apparatus (see for example Patent Document No. 2 and Patent Document No. 3).

There is also known, as a sterilization apparatus for grains or seeds, an apparatus that comprises a discharge-side electrode comprising a plurality of needle-shaped electrodes as provided; a ground-side electrode comprising a plate-shaped electrode, which is provided away from the above-mentioned discharge-side electrode and has a surface covered with an insulating plate; and a dielectric surrounding the above-mentioned discharge-side electrode and the above-mentioned ground-side electrode, in which sterilization targets such as grains or seeds are placed between the discharge-side electrode and the ground-side electrode and a pulsed streamer discharge is generated between the above-mentioned electrodes to sterilize them (see for example Patent Document No. 4 and Patent Document No. 5). In addition, there is also known an apparatus in which a plasma jet is irradiated to sterilize agricultural produces (see Patent Document No. 6).

With respect to the electrode used in the conventional plasma-generating apparatus, there have been proposed various kinds of electrodes, which are not intended to be used to sterilize agricultural products, but are used for surface processing for industrial material. There are known, for example, an electrode configuration using roll-type rotary electrodes so that a coating is formed on the surface of a substrate placed between the electrodes or a surface treatment for the substrate is conducted (see for example Patent Document No. 7), rotary electrodes in which a chemical reaction of a gas to be treated with a reaction gas is caused, with the use of rotation of rotary electrodes (see for example Patent Document No. 8), and rotary electrodes in which a plasma generated between rotary electrodes is discharged into an external space so that a substrate to be treated, placed in the external space is subject to a treatment (see for example Patent Document No. 9).

In addition to the above, with respect to the electrode used in the conventional plasma-generating apparatus, there are also known a configuration in which brush-type electrodes are used, which are not intended to be used to sterilize agricultural products, similarly to the mentioned electrodes (see for example Patent Document No. 10 and Patent Document 11), and there is also known a configuration in which the above-mentioned rotary electrodes is provided with this brush-type electrodes (see for example Patent Document No. 12 to Patent Document No. 14).

PRIOR ART DOCUMENT

Patent Document

[Patent Document 1] Japanese Patent Provisional Publication No. 2010-187648;
[Patent Document 2] Japanese Patent Provisional Publication No. 2013-172657;
[Patent Document 3] Japanese Patent Provisional Publication No. 2008-283909;
[Patent Document 4] Japanese Patent Provisional Publication No. 2000-295980;
[Patent Document 5] Domestic Republication No. 02/001971 of the PCT international application;
[Patent Document 6] Japanese Patent Provisional Publication No. 2008-237047;
[Patent Document 7] Japanese Patent Provisional Publication No. 2011-225954;
[Patent Document 8] Japanese Patent Provisional Publication No. 2002-28441;
[Patent Document 9] Japanese Patent Provisional Publication No. 2003-166062;
[Patent Document 10] Japanese Patent Provisional Publication No. H7-296993;
[Patent Document 11] Japanese Patent Provisional Publication No. 2003-38933;
[Patent Document 12] Japanese Patent Provisional Publication No. 2008-245784;

[Patent Document 13] Japanese Patent Provisional Publication No. H9-104985; and

[Patent Document 14] Japanese Patent Provisional Publication No. 2003-19785

DISCLOSURE OF THE INVENTION

Subject to be Solved by the Invention

However, the conventional plasma sterilization apparatus conducts sterilization with a rough intension by irradiating or injecting plasma to a sterilization target to conduct sterilization, with the result that, in case where there exist multiple sterilization targets and they have various three-dimensional shape, there is variability in degree of sterilization relative to individual sterilization targets, and even of sterilization capacity is the same, a degree of sterilization of a certain sterilization target may be so weak to provide an insufficient sterilization, or a degree of sterilization of a different kind of sterilization target may be so strong to cause a damage.

Such sterilization targets may include for example in agricultural products, citrus fruits such as orange, etc. with an outer skin, which is not edible, and strawberry, etc. with an outer skin, which is edible. In addition, such target may include avocado, pumpkin, etc. with an outer skin, which has non-uniform and distorted shape.

In case where sterilization targets have three-dimensional shapes on their surfaces, which are smooth, rough, distorted or uneven, as in agricultural products, sterilization utilizing plasma discharge with a constant intensity may provide areas in which sterilization is so strong and insufficient, respectively, in combination, thus leading to rough sterilization.

Even if where a plasma is generated with the use of electrodes with various kinds of shape, which are used in the conventional plasma-generating apparatus that is not intended to be used to sterilize agricultural products, to sterilize the agricultural products, an injection of plasma as generated may conduct a rough sterilization and provide areas in which sterilization is so strong and insufficient, respectively, in combination, thus leading to rough sterilization, in the same manner as mentioned above.

An object of the present invention has been made to solve the above-mentioned problems is to provide a plasma sterilization apparatus that permits plasma sterilization providing a uniform sterilization for even sterilization targets having various kinds of three-dimensional shape such as agricultural products, under mild conditions so as to prevent damage and quality deterioration of the targets.

Means to Solve the Subject

A plasma sterilization apparatus disclosed in the present application comprises a voltage-applying unit that applies a voltage to a sterilization target having conductivity; a pair of electrodes that apply, in a discharged state, the voltage applied by said voltage-applying unit to the sterilization target via a dielectric; and a position changing unit that changes a relative position between the pair of electrodes and the sterilization target.

In the plasma sterilization apparatus disclosed in the present application, the voltage-applying unit applies a voltage to a sterilization target having conductivity, the pair of electrodes apply, in a discharged state, the voltage applied by the voltage-applying unit to the sterilization target via a dielectric, and the position changing unit changes a relative position between the pair of electrodes and the sterilization target, in this manner. Accordingly, the dielectric via which the discharge is applied to the sterilization target permits to prevent the discharge from becoming an arc discharge. A position where the discharge is applied to the sterilization target sequentially varies, with the result that the discharge is caused, not locally but dispersively on the surface of the sterilization target. Such dispersive discharge permits to sterilize uniformly and gently the entire area of the surface of the sterilization target in a dry process, irrespective of the shape of the sterilization target (even if the sterilization target has a complicated shape such as a spherical body with an uneven shape). In addition, the discharge plasma, which is generated only on the part of the sterilization target, with which the dielectric comes into contact, permits to control an electric power required for applying the voltage, thus making it possible to conduct sterilization at a lower cost than sterilization with a continuous discharge.

Where appropriate, in the plasma sterilization apparatus disclosed in the present application, at least one of the pair of electrodes may comprise plural pairs of contact pieces which are provided, each of the contact pieces being flexible and comprising a conductor covered with a dielectric.

In such a configuration in which at least one of the pair of electrodes comprises plural pairs of contact pieces which are provided, each of the contact pieces is flexible and comprises a conductor covered with a dielectric, continuous movement with vibration of the contact pieces makes it possible to bring the contact pieces into contact with various positions of the sterilization target, so as to sterilize uniformly the entire area of the surface of the sterilization target without causing a local convergence. At the same time, contact of the contact piece with the sterilization target permits to wash the surface of the sterilization target.

Where appropriate, in the plasma sterilization apparatus disclosed in the present application, the dielectric may be formed of fiber, synthetic resin or silicone resin having a fiber form or a mesh form. In such a configuration in which the dielectric is formed of fiber, synthetic resin or silicone resin having a fiber form or a mesh form, the dielectric has a structure having a void space so that the void space is filled with a source gas for generating a plasma and the above-mentioned source gas is directly supplied to the conductors as the pair of electrodes covered with the dielectric, with the result that the above-mentioned sterilization target does not come into contact with the conductor due to the thickness of the dielectric, thus making it possible to conduct a gentle sterilization over the entire surface of the above-mentioned sterilization target.

Where appropriate, in the plasma sterilization apparatus disclosed in the present application, the position changing unit may move the sterilization target relative to the pair of electrodes. In such a configuration in which the position changing unit moves the sterilization target relative to the pair of electrodes, it is possible to bring surely each of the plurality of the sterilization targets into contact with the pair of electrodes so as to repeat contact with and separation from the pair of electrodes, thus leading to a dispersive sterilization, not a local sterilization and making it possible to sterilize uniformly and fully the sterilization targets.

Where appropriate, in the plasma sterilization apparatus disclosed in the present application, the position changing unit may rotate each of the contact pieces of which the pair of electrodes is composed, to bring at least front portion of at least one of the contact pieces into contact with the sterilization target.

In such a configuration in which the position changing unit rotates each of the contact pieces of which the pair of electrodes is composed, to bring at least front portion of at least one of the contact pieces into contact with the sterilization target, it is possible to secure a state in which all of the contact pieces move so as to be able to come into contact with the sterilization target, so that the contact pieces can come into full contact with all of a plurality of sterilization targets, thus making it possible to sterilize uniformly and fully the sterilization targets.

Where appropriate, the plasma sterilization apparatus disclosed in the present application may further comprise; a measurement unit that measures an impedance value of the sterilization target; and a control unit that controls change in the relative position provided by the position changing unit, based on the impedance value measured by the measurement unit.

In such a configuration in which the plasma sterilization apparatus comprises; a measurement unit that measures an impedance value of the sterilization target; and a control unit that controls change in the relative position provided by the position changing unit, based on the impedance value measured by the measurement unit, an amount of change in an optimum relative position is controlled in response to a kind of the sterilization target, based on the conductivities as measured of individual sterilization targets so that an optimum sterilization intensity can be determined in response to the kind of the sterilization target, thus making it possible to sterilize uniformly and fully the sterilization targets.

Where appropriate, in the plasma sterilization apparatus disclosed in the present application, the voltage-applying unit may change a voltage value to be applied, in response to a kind of the sterilization target. In such a configuration in which the voltage-applying unit changes a voltage value to be applied, in response to a kind of the sterilization target, it is possible to modulate a value of the voltage to be applied, also based on whether or not an outer skin of the sterilization target is edible, and the sterilization intensity can flexibly be changed by increasing the value of voltage as applied, for fruits such as orange an outer skin of which is not edible, since a higher intensity of sterilization may have priority over a damage of the outer skin, or by decreasing the value of voltage as applied, for fruits such as strawberry an outer skin of which is edible, so as to prevent a damage from occurring on it, thus making it possible to flexibly change the sterilization intensity to provide an optimum sterilization in response to a kind or characteristics of the sterilization target.

BRIEF DESCRIPTION OF THE DRAWINGS

FIG. 5A is an elevational view illustrating an electrode configuration of a plasma sterilization apparatus according to the fourth embodiment of the present invention;

FIG. 5B is an elevational view illustrating an electrode configuration of a plasma sterilization apparatus according to the fourth embodiment of the present invention;

EMBODIMENTS FOR CARRYING OUT THE INVENTION

First Embodiment of the Present Invention

Now, a plasma sterilization apparatus according to the first embodiment of the present invention will be described below with reference to FIG. 1.

Figure 1A:
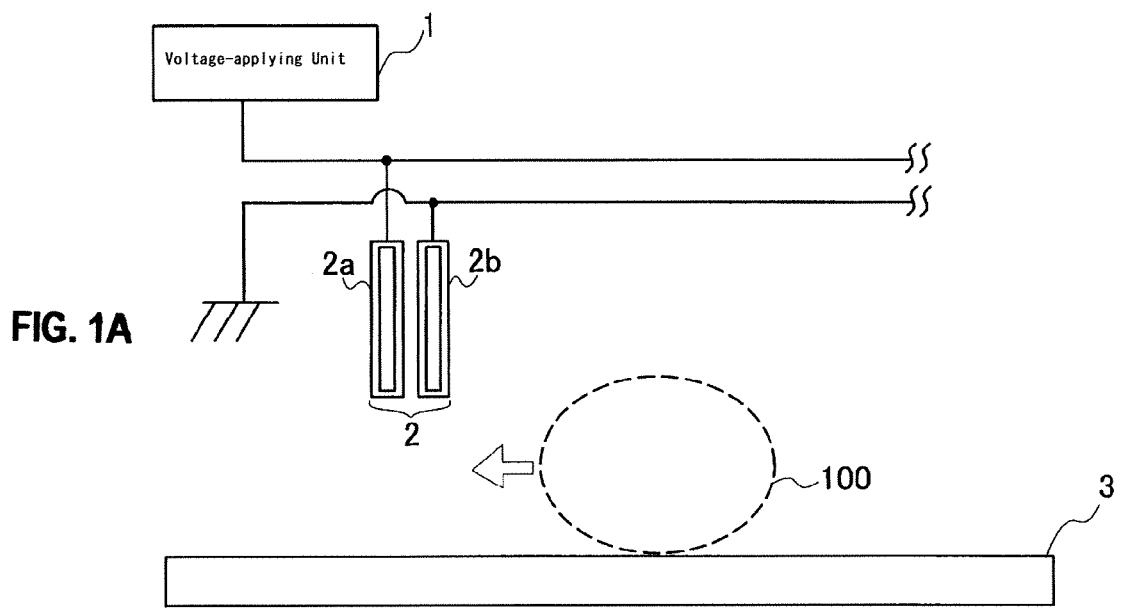
FIG. 1A is a configuration diagram illustrating a plasma sterilization apparatus according to the first embodiment of the present invention.
Figure 1B:
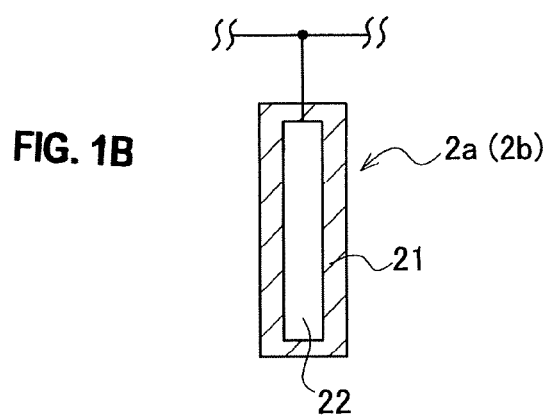
FIG. 1B is a configuration diagram illustrating a plasma sterilization apparatus according to the first embodiment of the present invention.

In FIG. 1(a), the plasma sterilization apparatus according to the first embodiment of the present invention comprises a voltage-applying unit 1 such as a power source that applies a voltage to a sterilization target 100 having conductivity; a pair of electrodes that apply, in a discharged state, the voltage applied by the voltage-applying unit 1 to the sterilization target 100 via a dielectric 21 (FIG. 1(b)); and a position changing unit 3 such as a conveyor that changes a relative position between the pair of electrodes 2 and said sterilization target 100. The above-mentioned pair of electrodes 2 is composed, as a pair of them, of one electrode 2a and another electrode 2b.

A source gas for plasma discharge is not limited only to the specific one. An ambient air may be used as it is, as the source gas. In this case, there is a benefit that sterilization can be conducted in an easy manner and at a low cost without preparing a specific gas. More specifically, an atmospheric air pressure suffices as a pressure condition for the plasma discharge.

Alternatively, a rare gas such as helium or argon may be used as the source gas. In this case there is a benefit that it is easy to cause discharge. It is preferable to use a mixed gas of the above-mentioned rare gas with air, nitrogen, oxygen or water vapor, and in this case, it is possible to increase the discharge area even at an atmospheric pressure to reduce the processing period of time.

The rare gas as used may be collected after use and separated to reuse it as a source gas for generating the discharge plasma. Depressurization with the use of a vacuum pump permits to further increase the discharge area to reduce the processing period of time.

The above-mentioned voltage-applying unit 1 may be used with a direct voltage or an alternating voltage, as long as difference in potential of each of the pair of electrodes 2 becomes constant even after a lapse of time, and namely each of voltages for the electrodes is fixed to any one of a high potential side or a low potential side. If the applied voltage is alternating, a low-frequency power source or a high-frequency power source (RF) may be used as the voltage-applying unit. There may be used, for example, an alternating-current source as the voltage-applying unit with a frequency band of several dozen Hz to hundreds Hz and with a voltage of 1 to 10 kV.

A configuration of the above-mentioned pair of electrodes 2 is not limited only to a specific one, as long as they are capable of coming into contact with the sterilization target 100 via the dielectric 21. However, it is preferable that the conductor 22 of which the pair of electrodes 2 is formed is covered with the dielectric 21.

The above-mentioned dielectric 21 is not limited only to a specific one, as long as it is material having a dielectric property, i.e., a high-resistance material.

The above-mentioned conductor 22 is not limited only to a specific one, as long as it is material having conductivity, and, for example, a metallic wire, conductive plastic, or carbon fiber may be used, and for example, a copper wire having flexibility may be used.

Figure 1C:
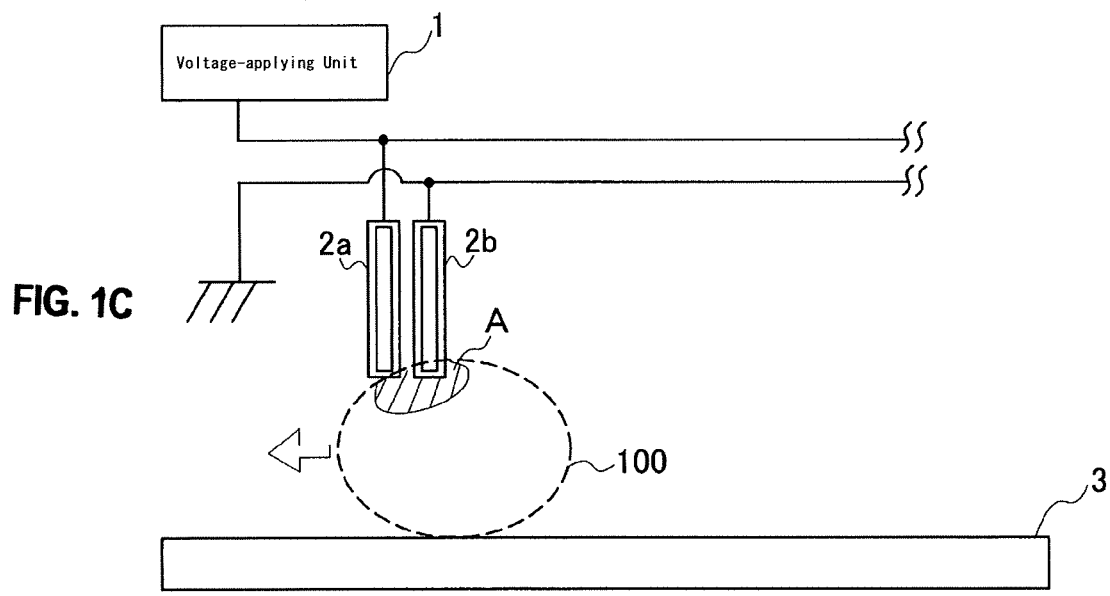
FIG. 1C is a configuration diagram illustrating a plasma sterilization apparatus according to the first embodiment of the present invention.

Referring to FIG. 1(c), the above-mentioned position changing unit 3 is not limited only to a specific one, as long as it changes a relative position between the pair of electrodes 2 and the sterilization target 100. In a preferable example, this unit moves the sterilization target 100 relative to the pair of electrodes 2, and there may be used a conveyor belt in which a moving belt can move the sterilization target 100 with a rolling motion, a roller conveyor in which rotation of a plurality of rotatable rollers can move the sterilization target 100 with a rolling motion, wind pressure, an inclined surface or vibration.

Such a change in a relative position permits to bring surely each of a plurality of sterilization targets 100 into contact with the pair of electrodes 2 so as to repeat contact with and separation from the pair of electrodes 2, thus leading to a dispersive sterilization, not a local sterilization and making it possible to sterilize uniformly and fully the sterilization targets 100. Thus, it is possible to conduct continuous discharge plasma processing relative to the plurality of sterilization targets 100 in an in-line state.

With a simple configuration in which the contact of the sterilization targets 100 to be subjected to the plasma sterilization with the pair of electrodes 2 causes the plasma discharge, the shape of the target is not limited only to a specific one, and this sterilization can be applied not only to a target having a simple three-dimensional shape, but also to a target having a complicated three-dimensional shape. It can be applied to, for example, agricultural products having complicated three-dimensional shapes on their surfaces, which are smooth, rough, distorted or uneven, for example, to citrus fruits such as orange, strawberry, avocado, pumpkin, or the like.

The voltage-applying unit 1 applies a voltage to the sterilization target 100, the pair of electrodes apply, in a discharged state, the voltage applied by the voltage-applying unit 1 to the sterilization target 100 via the dielectric 21; and the position changing unit 3 changes the relative position between the pair of electrodes 2 and said sterilization target 100, in this manner, with the result that the sterilization relative to the sterilization target 100 through the plasma discharge A is not of local convergence, but dispersive due to change in position where the discharge is given as shown in FIG. (c), and such dispersive discharge permits to sterilize uniformly and gently the entire area of the surface of the sterilization target, irrespective of the shape of the sterilization target 100 (even if the sterilization target has a complicated shape such as a spherical body with an uneven shape on the surface).

In addition, the discharge plasma, which is generated only on the part of the sterilization target 100, with which the dielectric 21 comes into contact, permits to generate a bare minimal discharge and control an overall electric power required for applying the voltage, thus making it possible to conduct sterilization at a lower cost than sterilization with a continuous discharge. Further, the discharge area on the surface of a certain sterilization target 100 is also changed, with the result that the entire area of the surface of this sterilization target 100 can be sterilized.

In case of agricultural products, for example, citrus fruits such as orange or the like, strawberry, avocado, pumpkin, or the like, as the sterilization targets 100, the sterilization as described above permits to sterilize/inactivate microorganism clinging to the surfaces of them, kill nematode and/or insects, and decompose pesticides, without using medical agents.

In the plasma sterilization apparatus according to the embodiment of the present invention, use of the gas having no residual performance in a plasma state makes it possible to inactivate disease agent, which may cause decay of the agricultural products or foods, without damaging the targets in this manner. Accordingly, this can contribute to a long storage standing in the way of the current export and import, and reduction of loss caused during a long distance transport. There is also a benefit that such an apparatus can widely be applied not only to agricultural products exported from Japan, but also agricultural products imported from foreign countries. In addition, "Safety of Food" is a high-priority issue whether at home or abroad, and there has been expanded, in many countries, a scale of cultivation of agricultural products cultivated based on a pesticide reduction program and organic agricultural products cultivated based on organic farming methods, as healthy and safe foods. Accordingly, the plasma sterilization apparatus according to the present invention, as the sterilization way without using pesticides, coincides with consumer preference, and objects to which the apparatus of the present invention can be applied, cover the wide range of the various kinds of agricultural products.

Second Embodiment of the Present Invention

Now, a plasma sterilization apparatus according to the second embodiment of the present invention will be described below.

The plasma sterilization apparatus according to the second embodiment of the present invention comprises the voltage-applying unit 1, the pair of electrodes 2, the dielectric 21, the conductor 22 and the position changing unit 3, as in the same manner as the first embodiment of the invention as described above, and further has a configuration in which any one of electrode of the one electrode 2a and the other electrode 2b of which the pair of electrodes 2 is composed, serves as the above-mentioned position changing unit 3. In such a configuration, the other electrode 2b facing to the one electrode 2a (of for example a sheet-shaped electrode) serves as the position changing unit 3, as shown in for example 2(a).

Figure 2A:
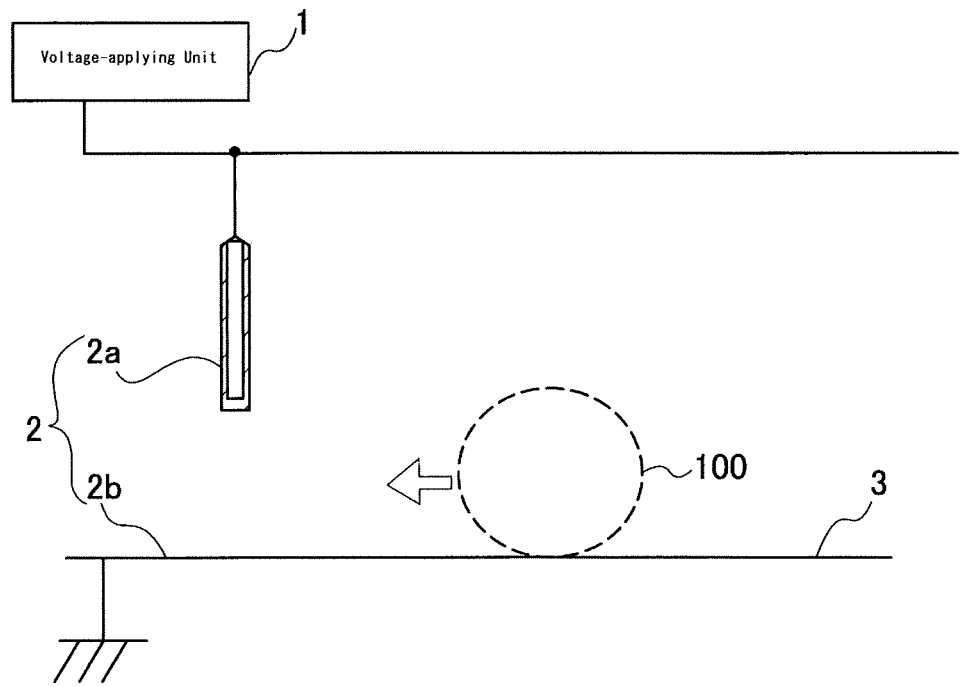
FIG. 2A is a configuration diagram illustrating a plasma sterilization apparatus according to the second embodiment of the present invention.
Figure 2B:
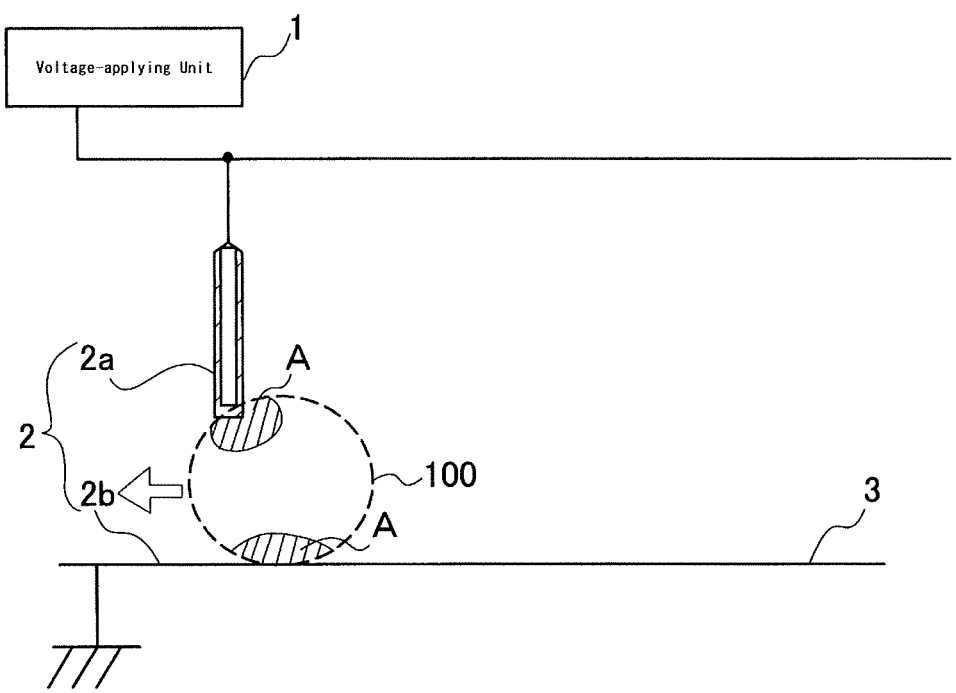
FIG. 2B is a configuration diagram illustrating a plasma sterilization apparatus according to the second embodiment of the present invention.

With such a configuration, the sterilization target 100, which is continuously moved by the position changing unit 3, can be subject to the plasma discharge A not only on the upper surface, but also the lower surface of the target, as shown in FIG. 2(b), thus making it possible to carry out a more effective and uniform sterilization over the entire surface of the sterilization target 100.

The above-mentioned position changing unit 3 may be composed not only as the unit having the sheet-shaped shape, but also as a roller conveyor in which a plurality of rollers having a cylindrical shape are placed side-by-side in a travelling direction of the sterilization target 100. In case where such a roller conveyor is used as the above-mentioned position changing unit 3, the contact areas of the rollers with the sterilization target 100 (namely, the areas where the plasma discharge A is given from the lower surface of the sterilization target 100) continuously and remarkably change, thus making it possible to carry out a more effective and uniform sterilization over the entire surface of the sterilization target 100.

As is clear also from the configuration as described above, in case where the material having the dielectric property is used as the material for the above-mentioned position changing unit 3 (a conveyor such as a conveyor belt or a roller conveyor), which faces the one electrode 2a (for example, the sheet-shaped electrode), the plasma can be generated on the both of the high pressure side (the one electrode 2a side) and the low pressure side (the conveyor side), on the one hand, and in case where the material having the conductive property is used, the strong plasma can be generated only on the high pressure side (the one electrode 2a side), on the other hand. Selection of the material on the low pressure side (the conveyor side) in response to the kind of the sterilization target 100 permits to achieve easily the optimum plasma processing in response to the kind of the sterilization target 100.

Third Embodiment of the Present Invention

Now, a plasma sterilization apparatus according to the third embodiment of the present invention will be described below.

Figure 3A:
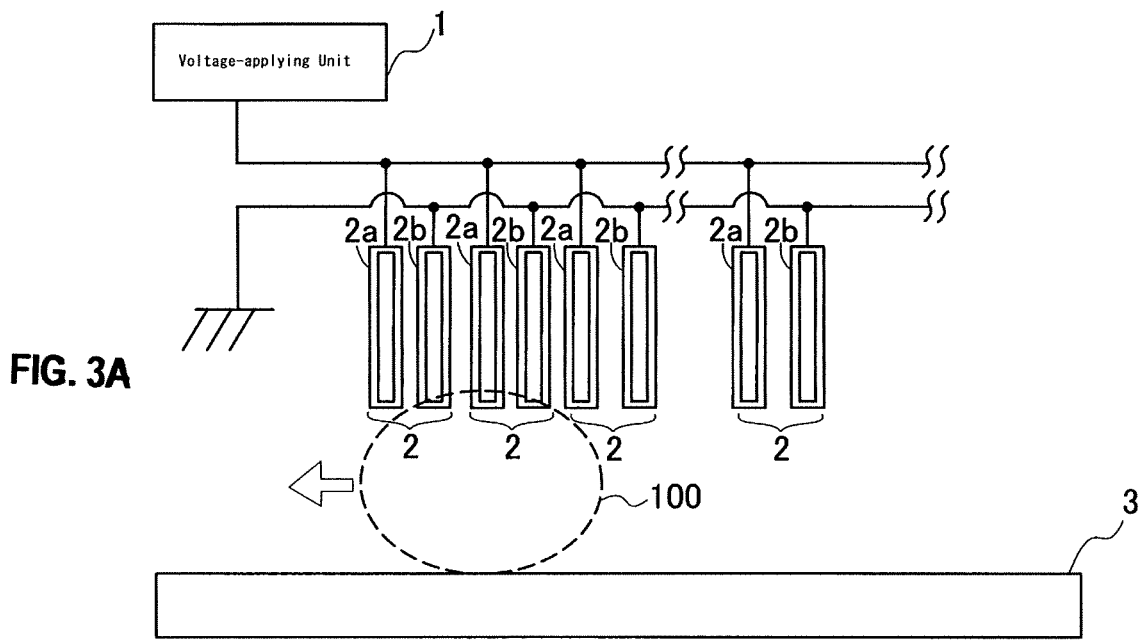
FIG. 3A is a configuration diagram illustrating a plasma sterilization apparatus according to the third embodiment of the present invention.

The plasma sterilization apparatus according to the third embodiment of the present invention comprises the voltage-applying unit 1, the pair of electrodes 2, the dielectric 21, the conductor 22 and the position changing unit 3, as in the same manner as the first embodiment of the invention as described above, and further has a configuration in which at least one of the pair of electrodes 2 comprises plural pairs of contact pieces which are provided, each of the contact pieces being flexible and comprises a conductor 22 covered with a dielectric 21, as shown in FIG. 3(a).

Figure 3B:
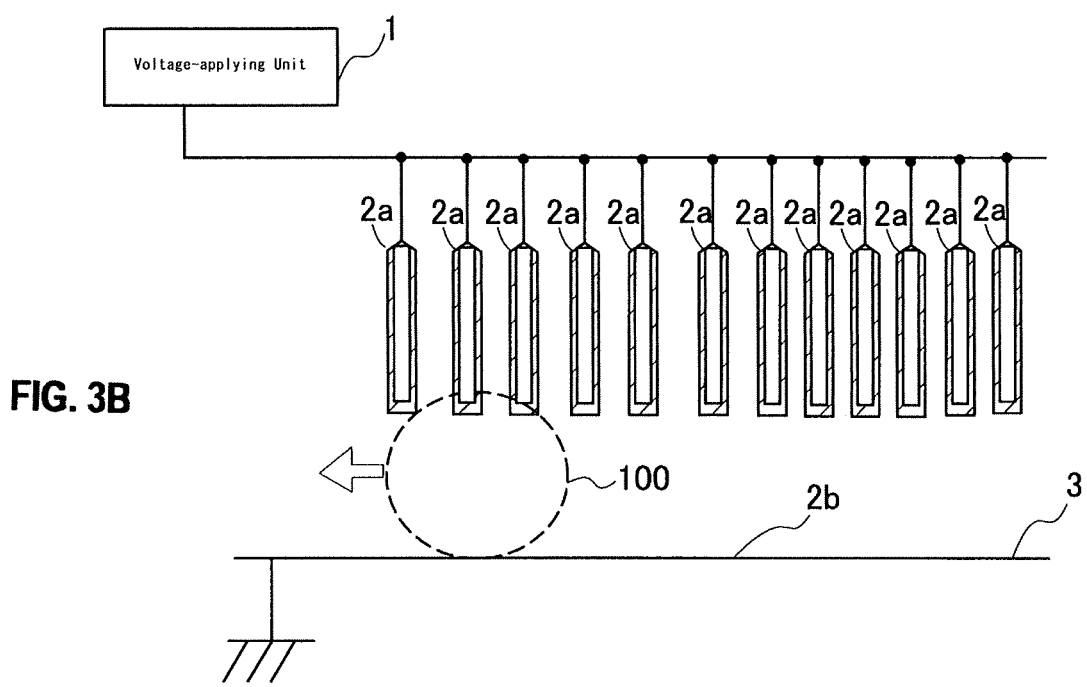
FIG. 3B is a configuration diagram illustrating a plasma sterilization apparatus according to the third embodiment of the present invention.

This embodiment of the present invention may be applied also to the plasma sterilization apparatus as described above according to the second embodiment of the present invention in the same manner as described above, as shown in FIG. 3(b).

Figure 4A:
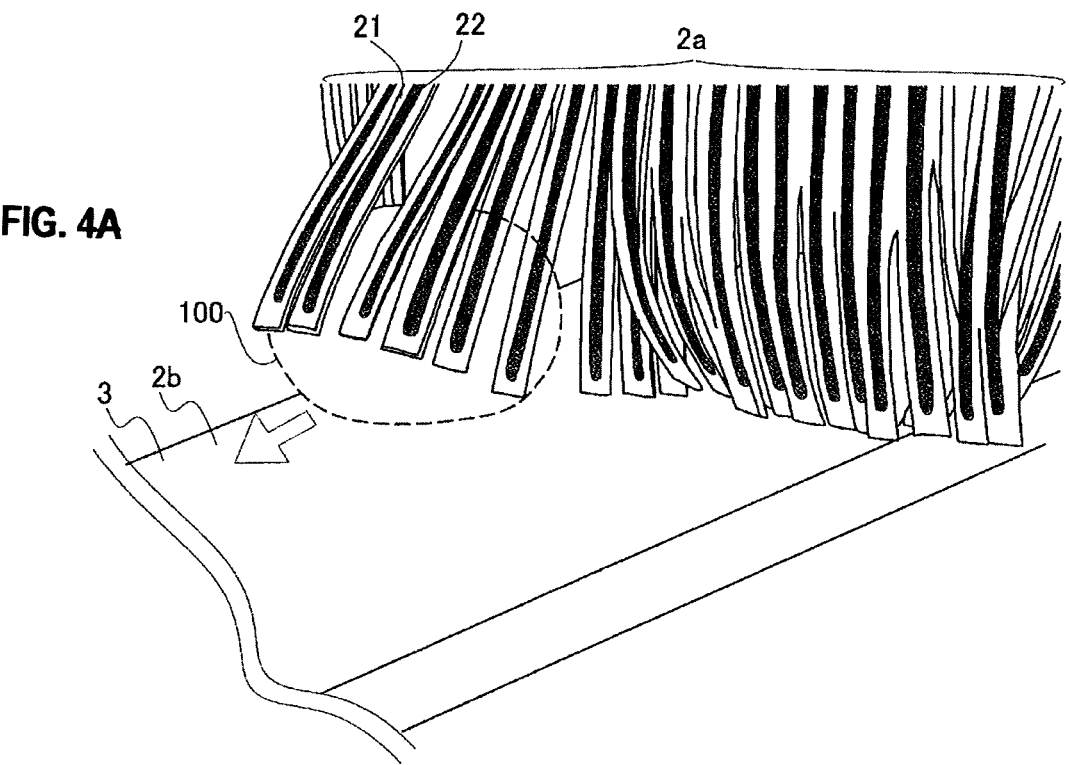
FIG. 4A is a perspective view illustrating a sterilization state with the use of the plasma sterilization apparatus according to the third embodiment of the present invention.
Figure 4B:
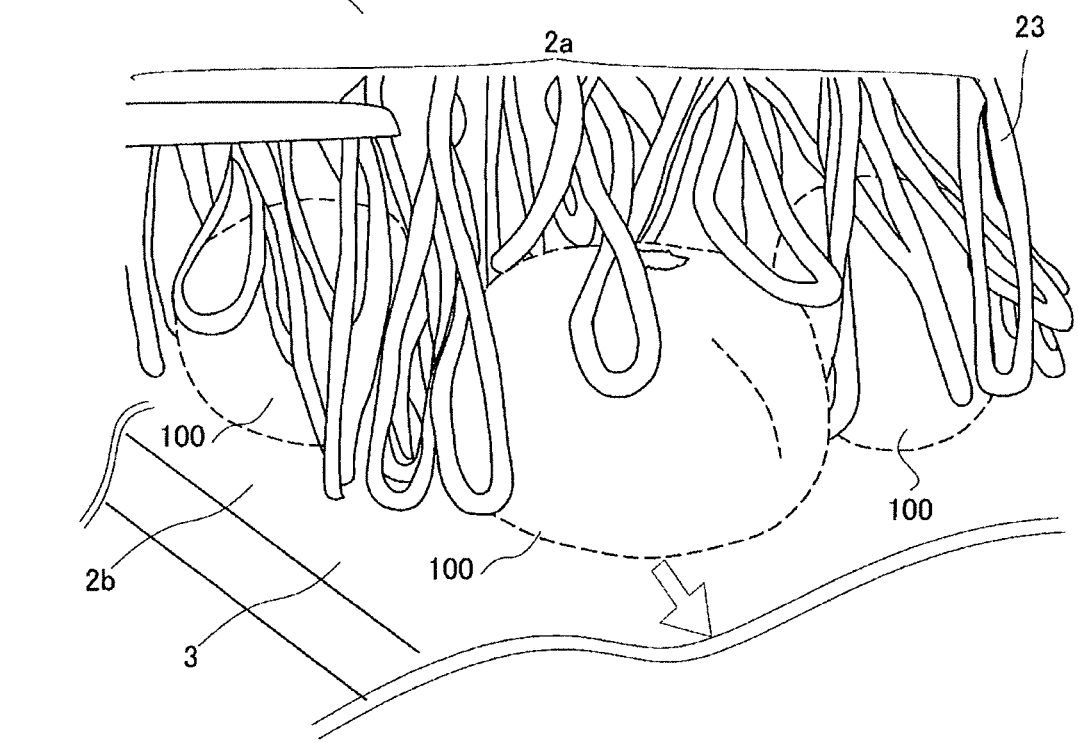
FIG. 4B is a perspective view illustrating a sterilization state with the use of the plasma sterilization apparatus according to the third embodiment of the present invention.

The shape of the contact piece 23 may not be limited only to a specific one. Each of the contact pieces 23 may for example be plate-shaped so that a plurality of contact pieces 23 forms a short split curtain as a whole, as shown in FIG. 4(a). This permits to increase the total area of the electrodes to increase the chance of contact with the sterilization target 100 and expand the discharge area. Alternatively, the contact piece 23 may have a string (rope) shape as shown in FIG. 4(b), and this permits to increase the total area of the electrodes so that the electrodes can reach every corner of the surface area of the sterilization target 100, thus making it possible to further expand the discharge area. String-shaped insulating bodies, which are easily available, may be used as they are, thus leading to a simple configuration of the apparatus.

In such a configuration, flexible and continuous movement of a plurality of contact pieces 23 makes it possible to bring the contact pieces 23 into contact with various positions of the sterilization target 100, so as to sterilize uniformly the entire area of the surface of the sterilization target 100 without causing a local convergence. In addition, a gentle contact of the flexible contact pieces 23 with the sterilization target 100 permits to conduct sterilization, while cleaning the surface of the sterilization target 100.

As is clear also from the configuration as described above, in case where the material having the dielectric property is used as the material for the above-mentioned position changing unit 3 (a conveyor such as a conveyor belt or a roller conveyor), which faces the one electrode 2a (the contact piece 23), the plasma can be generated on the both of the high pressure side (the contact piece 23) and the low pressure side (the conveyor side), on the one hand, and in case where the material having the conductive property is used, the strong plasma can be generated only on the high pressure side (the contact piece 23), on the other hand. Selection of the material on the low pressure side (the conveyor side) in response to the kind of the sterilization target 100 permits to achieve easily the optimum plasma processing in response to the kind of the sterilization target 100.

Fourth Embodiment of the Present Invention

Now, a plasma sterilization apparatus according to the fourth embodiment of the present invention will be described below.

The plasma sterilization apparatus according to the fourth embodiment of the present invention comprises the voltage-applying unit 1, the pair of electrodes 2, the dielectric 21, the conductor 22 and the position changing unit 3, as in the same manner as the first embodiment of the invention as described above, and further has a configuration in which the dielectric 21 is formed of fiber, synthetic resin or silicone resin having a fiber form or a mesh form.

The material for the dielectric 21 is of a porous body having a void space, as shown in FIG. 5(a). The fiber may include ultrafine fiber, carbon fiber, or the like. The synthetic resin may include soft plastic resin, fluorine resin, or the like.

The void space formed in this dielectric 21 permits the source gas (or an air layer), which serves as material for generating the plasma, to penetrate into this void space so that the dielectric is filled with the source gas, and this source gas is directly supplied to the conductors 22 as the pair of electrodes 2 covered with this dielectric 21, in this manner. Accordingly, the plasma discharge is surely caused relative to the sterilization target 100 coming into contact with this dielectric 21, as shown in FIG. 5(a), thus making it possible to sterilize surely the surface of the sterilization target 100 coming into contact with this dielectric 21. On the other hand, the thickness of this dielectric 21 prevents the sterilization target 100 from directly coming into contact with the conductor 22, thus making it possible to conduct a gentle sterilization over the entire surface of the above-mentioned sterilization target 100.

There may be adopted a configuration in which the apparatus is provided with the second conductor 22a, which has a hollow tubular-shape and is provided to surround the above-mentioned conductor 22 spaced apart from it, as the electrode to which the voltage is to be applied, of one electrode 2a and the other electrode 2b of which the above-mentioned pair of electrodes 2 are composed, so that only when the above-mentioned conductor 22 and the second conductor 22a come into contact with each other, the voltage as applied is kept in a conduction state to generate the plasma discharge.

In such a configuration, the electrode to which the voltage is to be applied, of the above-mentioned pair of electrodes 2, is pressed against the sterilization target 100 and the conductor 22 and the second conductor 22a (FIG. 5(b)) come into contact with each other, and at this time the plasma discharge is finally caused, with the result that the discharge relative to the sterilization target 100 is caused selectively and surely, thus permitting to restrict consumption of electricity and conduct an effective sterilization.

The feature of this embodiment of the present invention may be applied to each of the second and third embodiments of the present invention, and in any one of the cases, the thickness of the above-mentioned dielectric 21 having the configuration with the void space prevents the sterilization target 100 from directly coming into contact with the conductor 22, and the conductor 22 protects the sterilization target 100 from a strong direct discharge, thus making it possible to conduct a gentle sterilization over the entire surface of the sterilization target 100, Fifth Embodiment of the Present Invention Now, a plasma sterilization apparatus according to the fifth embodiment of the present invention will be described below, with reference to FIG. 6 to FIG. 9.

Figure 6:
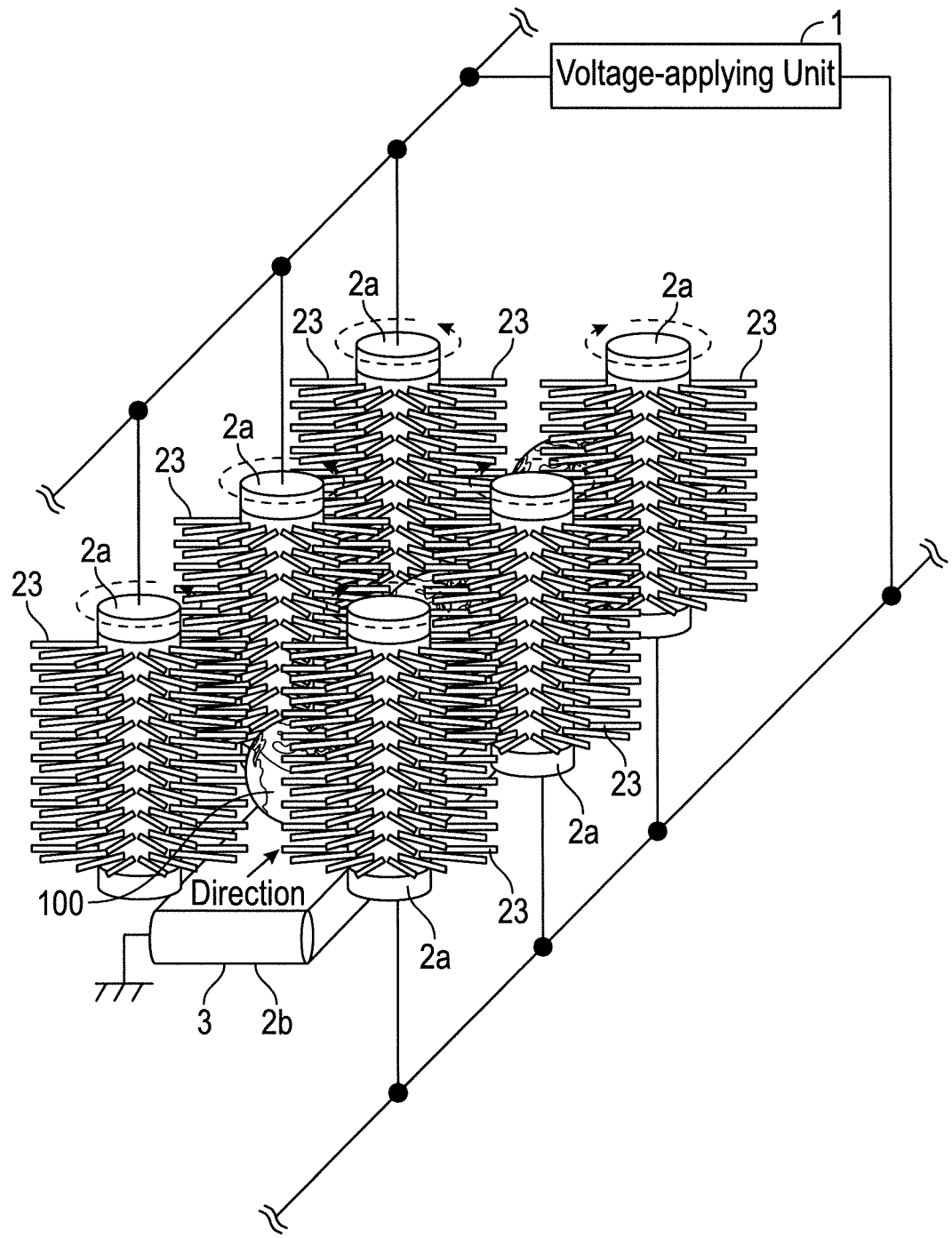
FIG. 6 is a configuration diagram illustrating a plasma sterilization apparatus according to the fifth embodiment of the present invention.
Figure 7:
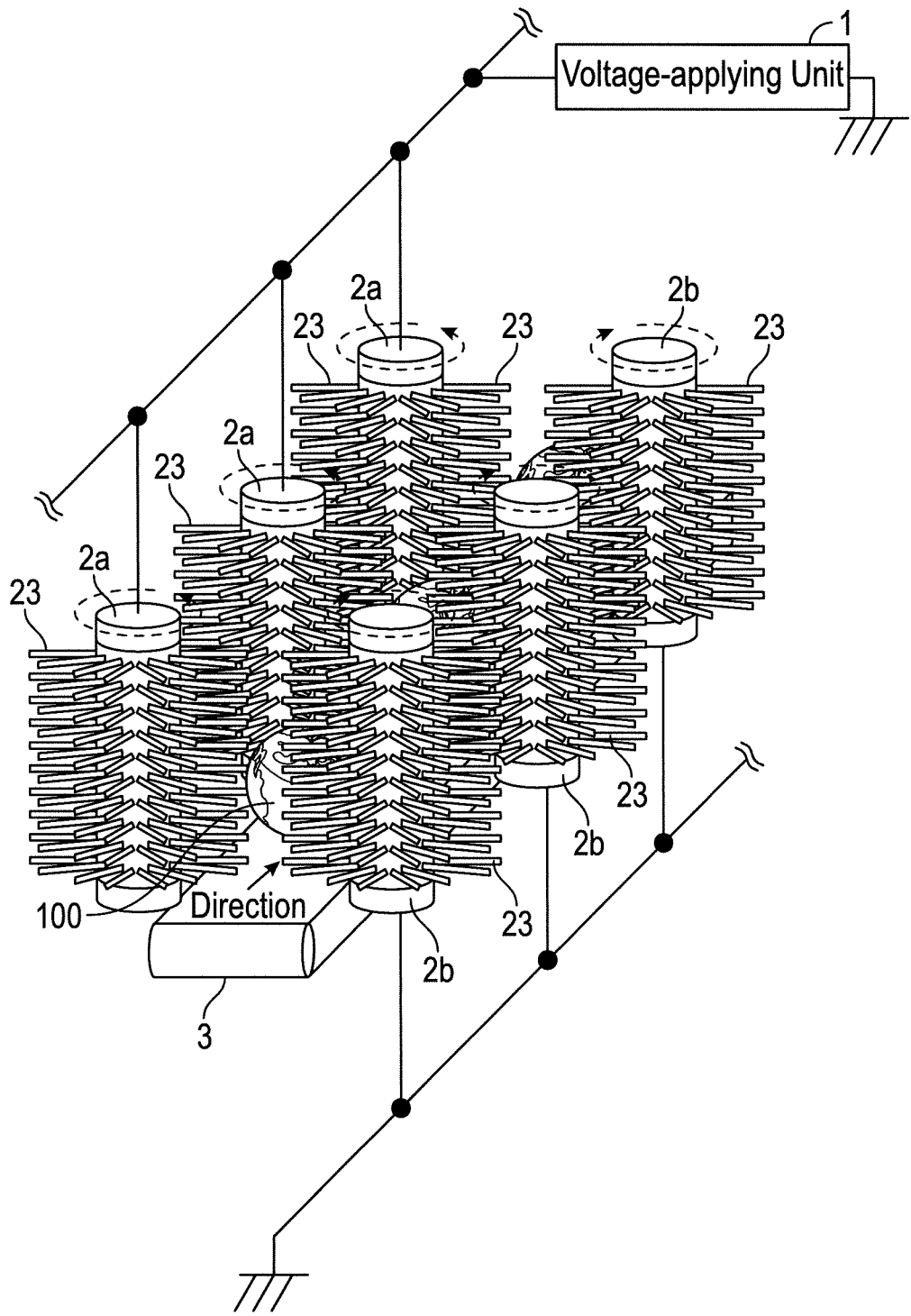
FIG. 7 is a configuration diagram illustrating a plasma sterilization apparatus according to the fifth embodiment of the present invention.

The plasma sterilization apparatus according to the fifth embodiment of the present invention comprises the voltage-applying unit 1, the pair of electrodes 2, the dielectric 21, the conductor 22, the contact pieces 23 and the position changing unit 3, as in the same manner as the third embodiment of the invention as described above, and further has a configuration in which the above-mentioned position changing unit 3 rotates each of the contact pieces 23, which compose the pair of electrodes 2 to bring at least front portion of at least one of the contact pieces 23 into contact with the sterilization target 100, as shown in FIG. 6 and FIG. 7. FIG. 6 corresponds to FIG. 3(a) of the third embodiment of the present invention, FIG. 7 corresponds to FIG. 3(b) of the third embodiment of the present invention, and each of these figures shows a configuration in which the sterilization target 100 can be sterilized in an in-line state.

Figure 8A:
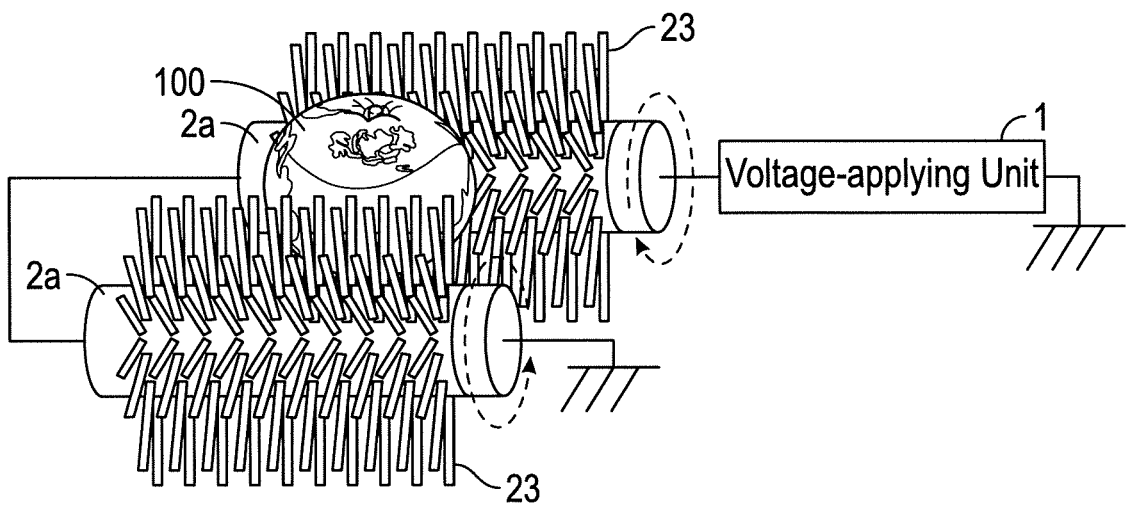
FIG. 8A illustrates a modification of the plasma sterilization apparatus according to the fifth embodiment of the present invention, and an example of the shape of contact pieces.
Figure 8B:
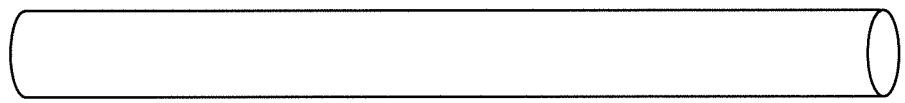
FIG. 8B illustrates a modification of the plasma sterilization apparatus according to the fifth embodiment of the present invention, and an example of the shape of contact pieces.
Figure 8C:
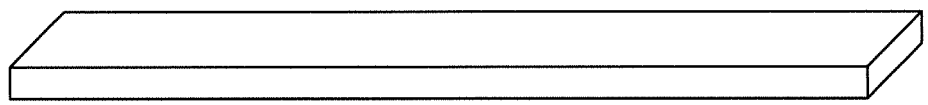
FIG. 8C illustrates a modification of the plasma sterilization apparatus according to the fifth embodiment of the present invention, and an example of the shape of contact pieces.
Figure 8D:
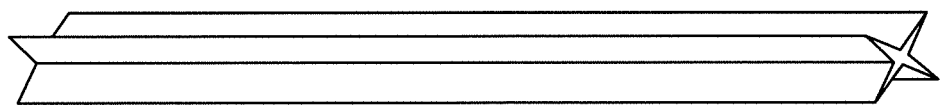
FIG. 8D illustrates a modification of the plasma sterilization apparatus according to the fifth embodiment of the present invention, and an example of the shape of contact pieces.
Figure 8E:
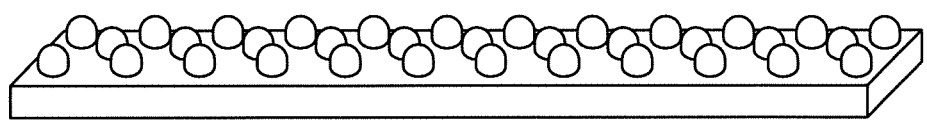
FIG. 8E illustrates a modification of the plasma sterilization apparatus according to the fifth embodiment of the present invention, and an example of the shape of contact pieces.

As other configuration than the in-line processing, there may be adopted a configuration in which a continuous sterilization processing is conducted while holding the sterilization target 100 between a pair of electrodes 2 with the contact pieces 23, as shown in FIG. 8(a).

The shape of the contact pieces 23 is not limited only to the specific one. Various shapes such as a cylindrical shape, a plate shape, an asteroid shape in cross section, a concavo-convex shape, or the like may be used as shown in FIGS. 8(b) to 8(e), and an optimum shape may be selected in response to a surface shape of the sterilization target 100 and an extent of sterilization, and for example, the contact pieces 23 having the asteroid shape in cross section is selected for, for example, avocado having a distorted shape, or the like.

It is possible to secure a state in which all of the contact pieces 23 move so as to be able to come into contact with the sterilization target 100, so that the contact pieces 23 can come into full contact with all of a plurality of sterilization targets 100, thus making it possible to sterilize uniformly and fully the sterilization targets 100, in this manner.

Figure 9A:
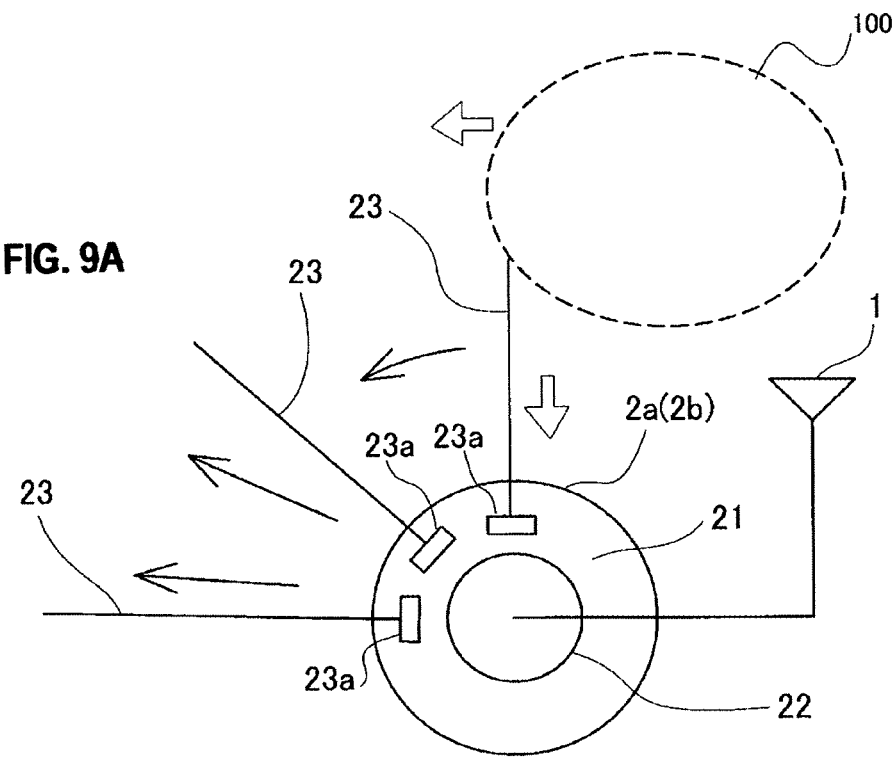
FIG. 9A is a configuration diagram illustrating a modification of the electrode configuration of the plasma sterilization apparatus according to the fifth embodiment of the present invention.

A modification of this contact pieces 23, there may be applied a configuration in which each of contact pieces 23, which are provided around one electrode of the pair of electrodes 2, spaced apart from the conductor 22 of this electrode, is provided on its conductor 22 side with a movable conductor 23a, as shown in FIG. 9(a). This movable conductor 23a provides a switching function of electric conduction in which it is not until this movable conductor 23a comes into contact with the conductor 22 that the voltage from the voltage-applying unit 1 is applied to the conductor 22.

Figure 9B:
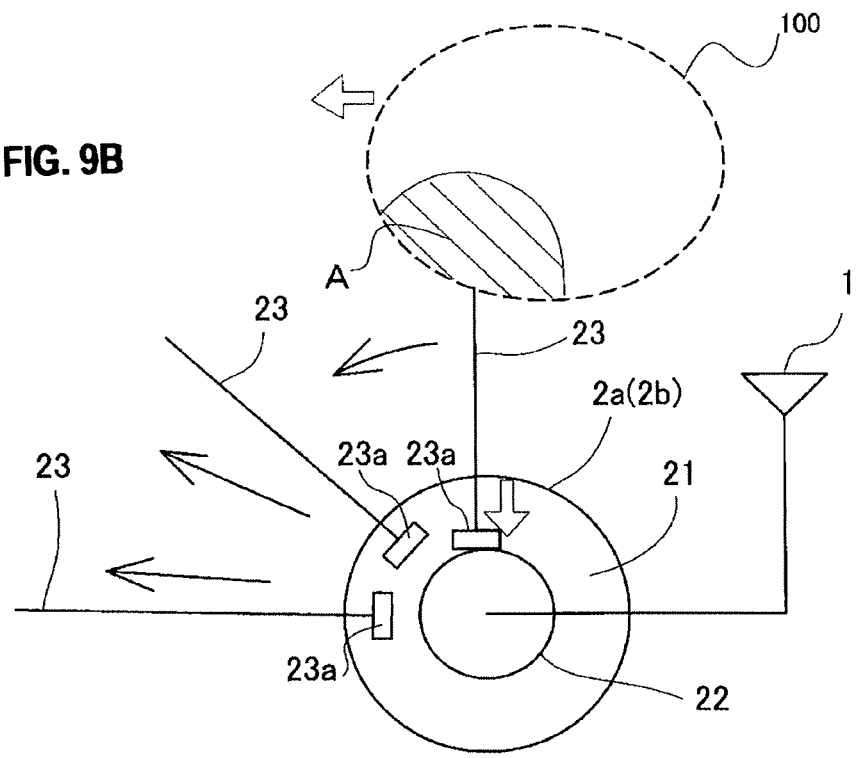
FIG. 9B is a configuration diagram illustrating a modification of the electrode configuration of the plasma sterilization apparatus according to the fifth embodiment of the present invention.

In this configuration in which, at the time when the contact piece 23 comes into contact with the sterilization target 100, the switching function of electric conduction is activated by the contact of the movable conductor 23a with the conductor 22 as shown in FIG. 9(b), with the result that the voltage from the voltage-applying unit 1 is applied to the conductor 22 to generate the plasma discharge, with the result that the discharge relative to the sterilization target 100 is caused selectively and surely, thus permitting to restrict consumption of electricity and conduct an effective sterilization.

The feature of this embodiment of the present invention may be applied to the fourth embodiment of the present invention as described above, and in this case, the configuration of the rotation of the respective contact pieces 23 bring the contact pieces 23 into full contact with a plurality of sterilization targets 100, thus making it possible to sterilize uniformly and fully the sterilization targets, in the same manner as this present embodiment of the present invention.

Sixth Embodiment of the Present Invention

Figure 10A:
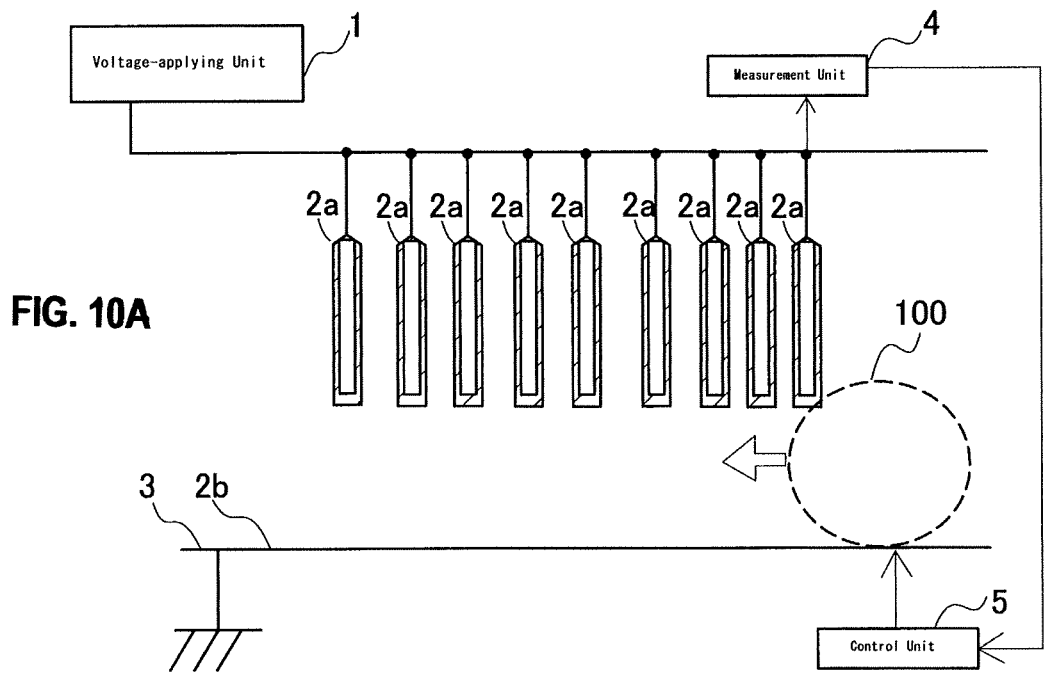
FIG. 10A is a configuration diagram illustrating a plasma sterilization apparatus according to the sixth embodiment of the present invention.

Now, a plasma sterilization apparatus according to the sixth embodiment of the present invention will be described below with reference to FIG. 10(a).

The plasma sterilization apparatus according to the sixth embodiment of the present invention comprises the voltage-applying unit 1, the pair of electrodes 2, the dielectric 21, the conductor 22, the contact pieces 23 and the position changing unit 3, as in the same manner as the third embodiment of the invention as described above, and further comprises a measurement unit 4 that measures an impedance value of the sterilization target 100; and a control unit 5 that controls change in the relative position provided by the position changing unit 3, based on the impedance value measured by the measurement unit 4.

This measurement unit 4 can measure the impedance value at the time when the first contact with the sterilization target 100 is made, and thereafter, the control unit 5 controls change in the relative position provided by the position changing unit 3, based on the impedance value the thus measured. For example, in a case of the sterilization target 100 having the high impedance value, it is possible to conduct a full sterilization over time by decreasing an amount of change in the relative position provided by the position changing unit 3 (by decreasing the rate of movement). For example, in a case of the sterilization target 100 having the low impedance value, it is possible to conduct a mild sterilization without damaging the surface by increasing an amount of change in the relative position provided by the position changing unit 3 (by increasing the rate of movement).

The amount of change in an optimum relative position is controlled in response to a kind of the sterilization target 100, based on the conductivities as measured of individual sterilization targets 100 so that the optimum sterilization intensity can be determined in response to the kind of the sterilization target 100, thus making it possible to sterilize uniformly and fully the sterilization targets 100.

The feature of this embodiment of the present invention may be applied to the first, second, fourth and fifth embodiments of the present invention as described above, and in any one of the cases, the amount of change in the relative position provided by the position changing unit 3 is controlled based on the impedance value as measured so that an optimum sterilization intensity can be determined in response to the kind of the sterilization target 100, thus making it possible to sterilize uniformly and fully the sterilization targets 100.

Seventh Embodiment of the Present Invention

Now, a plasma sterilization apparatus according to the seventh embodiment of the present invention will be described below with reference to FIG. 10(b).

Figure 10B:
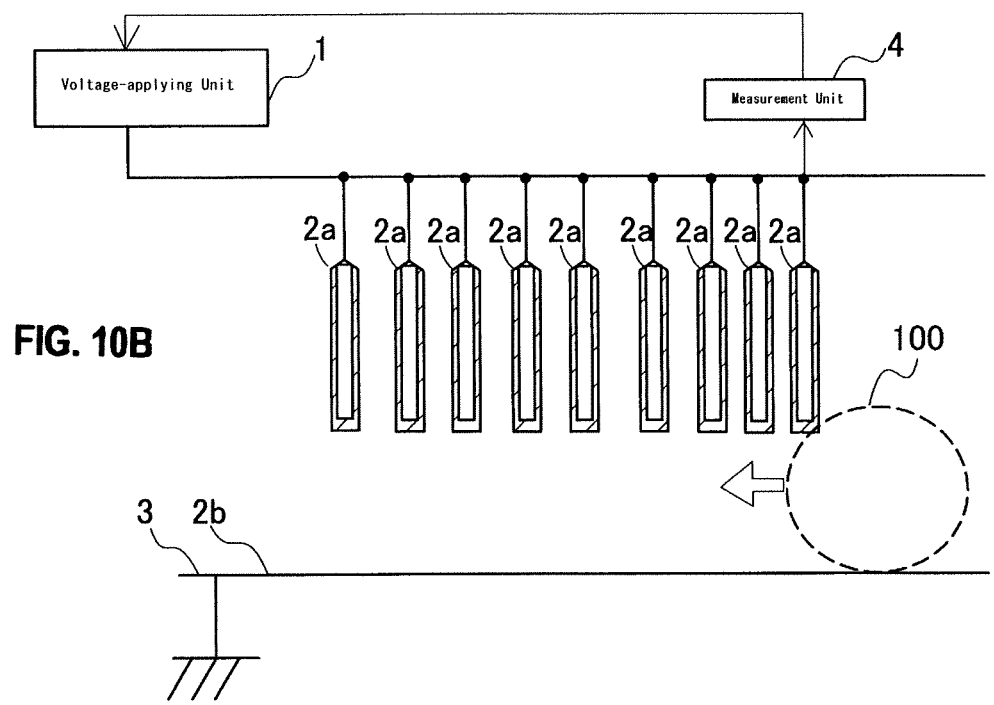
FIG. 10B is a configuration diagram illustrating a plasma sterilization apparatus according to the seventh embodiment of the present invention.

The plasma sterilization apparatus according to the seventh embodiment of the present invention comprises the voltage-applying unit 1, the pair of electrodes 2, the dielectric 21, the conductor 22, the contact pieces 23, the position changing unit 3 and the measurement unit 4, as in the same manner as the sixth embodiment of the invention as described above, and further has a configuration in which the voltage-applying unit 1 changes, in place of the above-mentioned control unit 5, a voltage value to be applied, based on the impedance value as measured by the measurement unit 4, as shown in FIG. 10(b).

More specifically, in such a configuration, the kind of sterilization target 100 is determined based on the impedance value as measured, and the above-mentioned voltage-applying unit 1 changes the voltage value to be applied, in response to the kind of sterilization target 100.

The above-mentioned voltage-applying unit 1 changes the voltage value to be applied, in response to the kind of sterilization target 100, in this manner, thus making it possible to flexibly and individually change the sterilization intensity to conduct sterilization in response to a kind or characteristics of the sterilization target 100.

The feature of this embodiment of the present invention may be applied to the first to fifth embodiments of the present invention as described above. More specifically, in the configuration in which the voltage-applying unit 1 changes a voltage value to be applied, in response to a kind of the sterilization target 100, it is possible to modulate a value of the voltage to be applied, also based on whether or not an outer skin of the sterilization target 100 is edible, and the sterilization intensity can flexibly be changed by increasing the value of voltage as applied, for fruits such as orange an outer skin of which is not edible, since a higher intensity of sterilization may have priority over a damage of the outer skin, or by decreasing the value of voltage as applied, for fruits such as strawberry an outer skin of which is edible, so as to prevent a damage from occurring on it, thus making it possible to flexibly change the sterilization intensity to provide sterilization in response to a kind or characteristics of the sterilization target 100.

Examples of the present invention will be described below, but they only exemplify the plasma sterilization apparatus according to the present invention and the present invention is not limited only to such examples.

Example No. 1

Sterilization of a sterilization target was conducted by the use of the apparatus according to the third embodiment of the present invention as described above. With respect to experimental conditions, an alternating high voltage (10 kVpp, 10 kHz) was applied to a plurality of string-shaped electrodes (hereinafter also referred to as the "sheet-shaped electrode"), which were formed as flexible contact pieces by covering the pair of electrodes formed of a metallic wire with silicone resin as dielectric, so as to generate plasma to sterilize directly spore of *Penicillium digitatum* on a fruit skin of *Citrus unshiu*. Spore of *Penicillium digitatum* as suspended ($4\times10^7$/ml) was splayed on *Citrus unshiu* as the sterilization target and subjected to a plasma irradiation for 0 to 10 seconds. The sterilization effect by the plasma irradiation was assessed by wiping up spore of *Penicillium digitatum* in an area which was subjected to the plasma irradiation, incubating them on culture media, and counting the number of colonies.

Figure 11A:
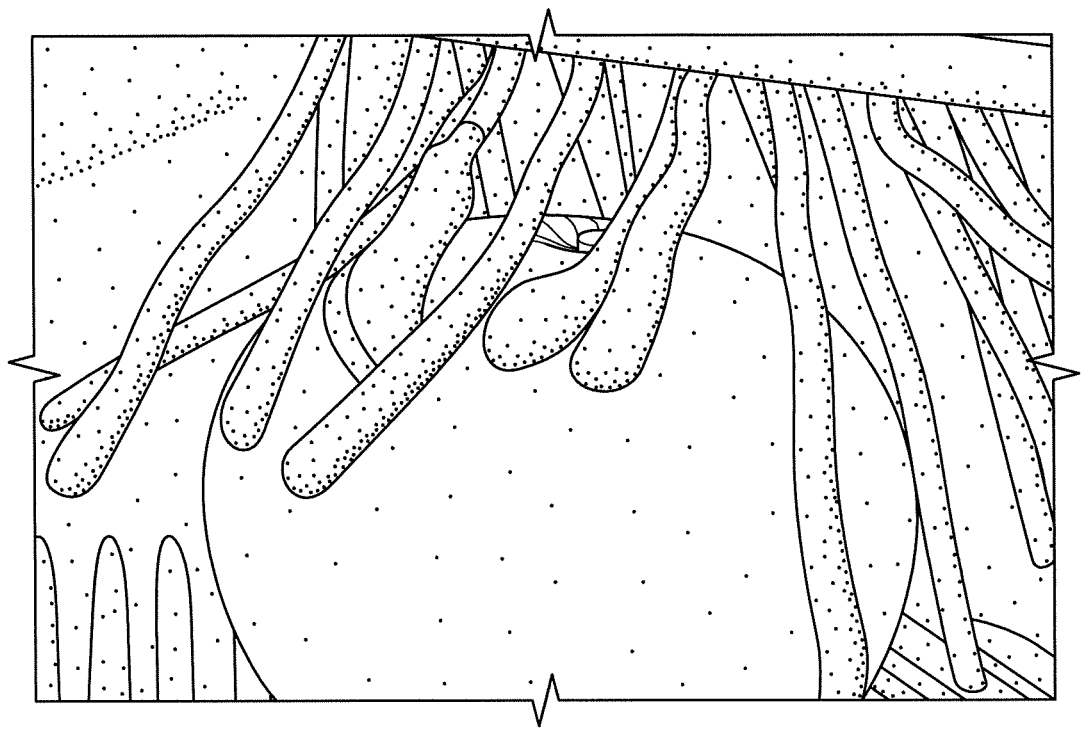
FIG. 11A is a perspective view of a discharge state the plasma sterilization apparatus according to Example No. 1 of the invention.
Figure 11B:
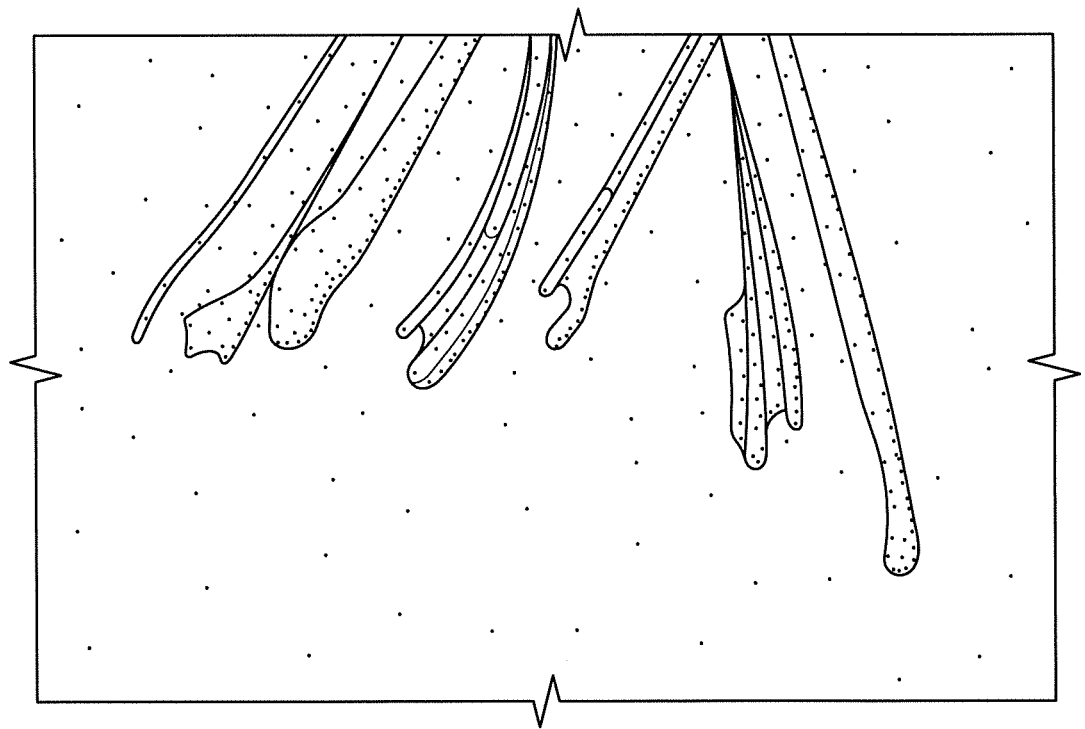
FIG. 11B is a perspective view of a discharge state the plasma sterilization apparatus according to Example No. 1 of the invention.

A state of the above-mentioned discharge is shown in FIG. 11(*a*). It was confirmed that the string-shaped contact pieces were brought into contact with the orange of agricultural products, as the sterilization target, as shown in FIG. 11(*a*), and the discharge was generated only in a place where the orange and the contact pieces came into contact with each other, as shown in FIG. 11(*b*).

Figure 12A:
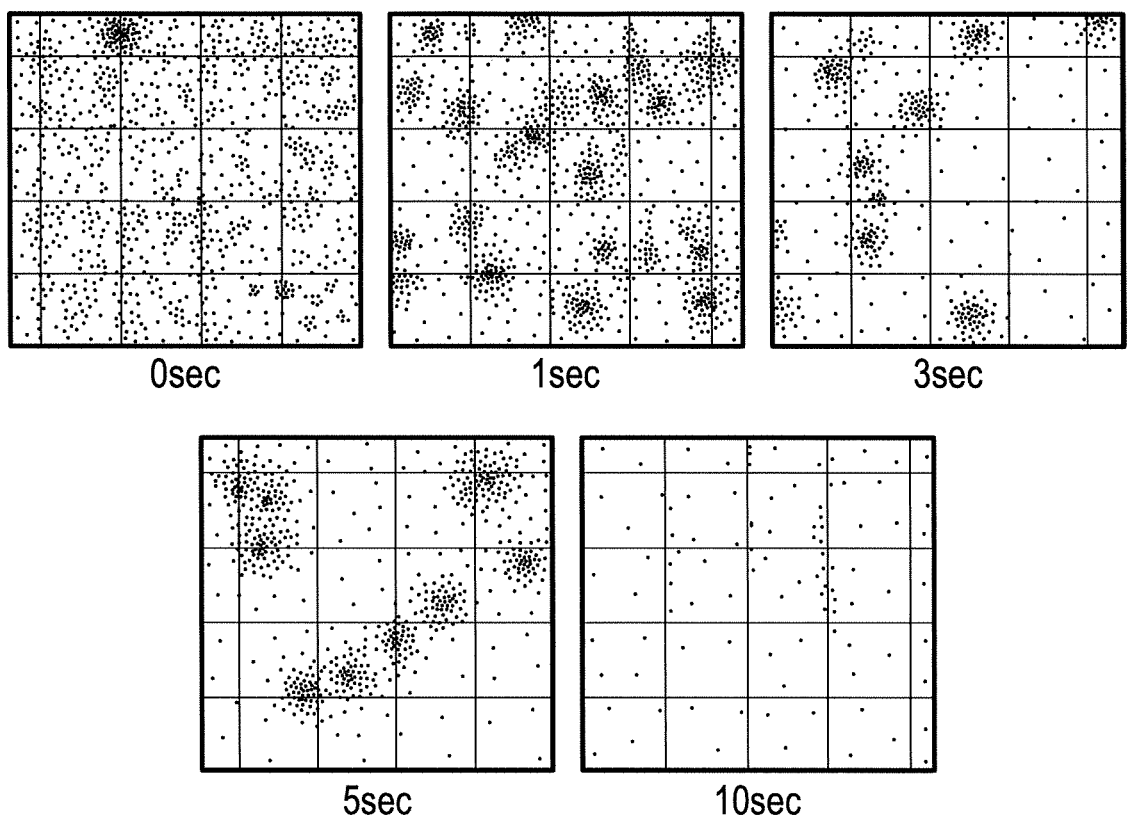
FIG. 12A is a diagram showing sterilization results by the plasma sterilization apparatus of the plasma sterilization apparatus according to Example No. 1 of the invention, and a graph showing a number of residual fungi relative to a plasma processing period of time.
Figure 12B:
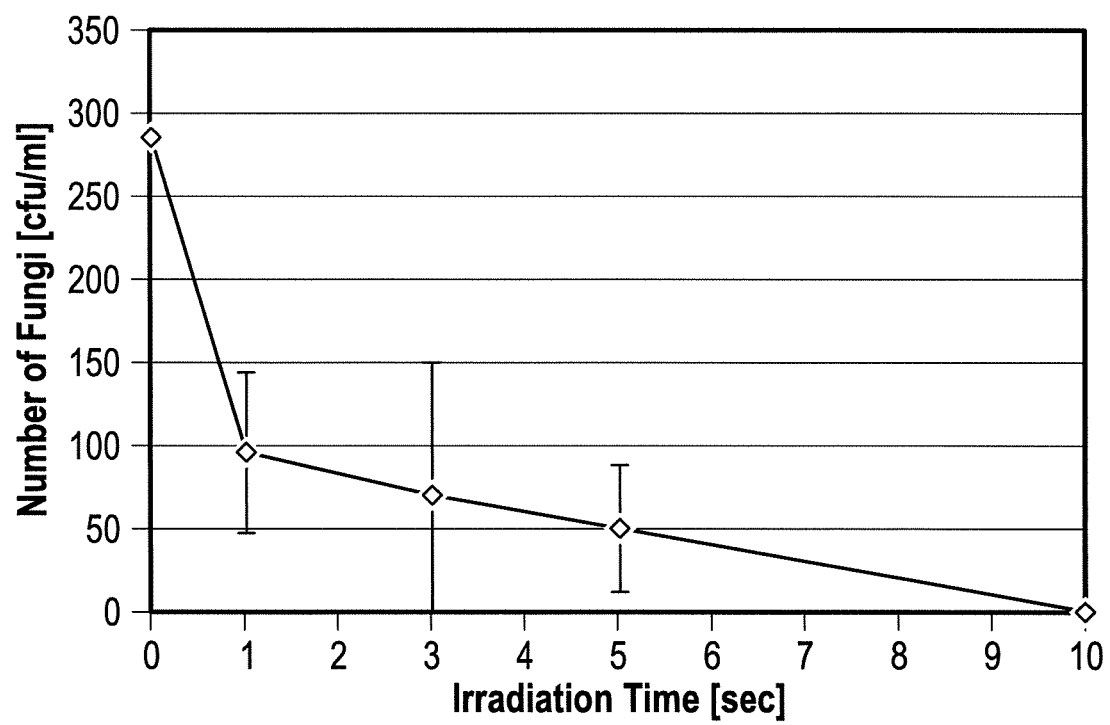
FIG. 12B is a diagram showing sterilization results by the plasma sterilization apparatus of the plasma sterilization apparatus according to Example No. 1 of the invention, and a graph showing a number of residual fungi relative to a plasma processing period of time.

With respect to the sterilization effects obtained by the above-mentioned discharge, it is shown in FIG. 12(*a*) the degree of sterilization relative to the plasma processing period of time and a graph showing a number of residual fungi relative to a plasma processing period of time (based on the number of colonies as counted) of FIG. 12(*b*) that the residual fungi remarkably reduced after a lapse of 1 second of the irradiation time, and a full sterilization was conducted by the irradiation for about 10 seconds.

Figure 13A:
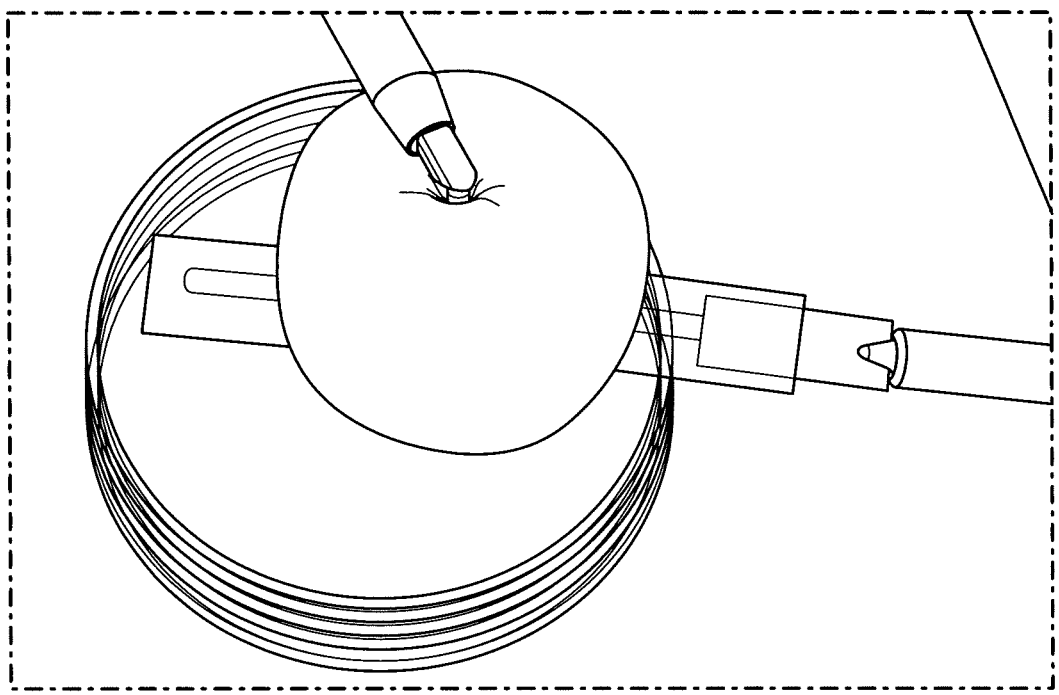
FIG. 13A is a perspective view showing experiment conditions by the plasma sterilization apparatus according to Example No. 1 of the invention.
Figure 13B:
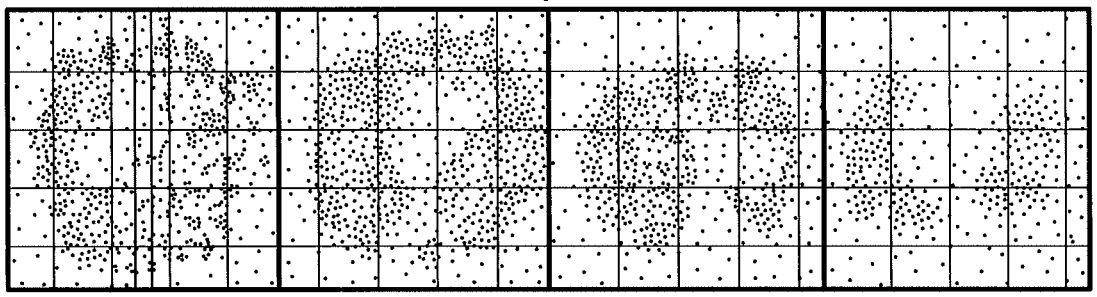
FIG. 13B is a diagram showing a sterilization range for a sheet-shaped electrode having a width of 3 mm.
Figure 13C:
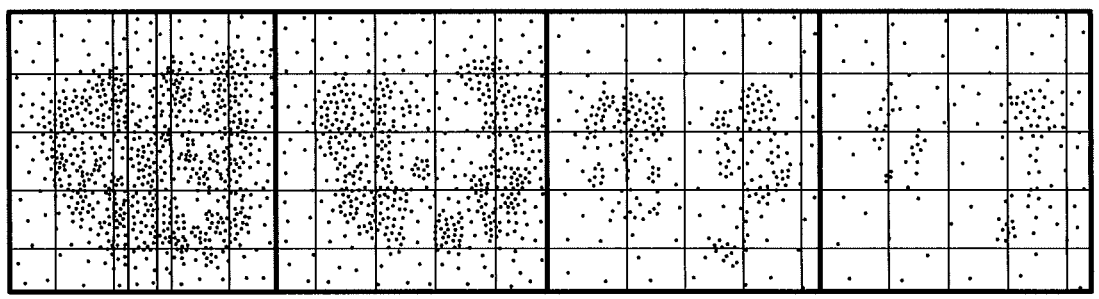
FIG. 13C is a diagram showing a sterilization range for a sheet-shaped electrode having a width of 3 mm, and a photograph (c) showing a sterilization range for a sheet-shaped electrode having a width of 5 mm.

Further, there was confirmed the sterilization range by the sheet-shaped electrodes used in the above-mentioned apparatus. Two types of the sheet-shaped electrodes having the width of 3 mm and the width of 5 mm were prepared, and *Citrus unshiu* was brought into contact with each of the sheet-shaped electrodes as shown in FIG. 13(*a*) and the voltage was applied under the following experimental conditions, and then, the sterilization status after a lapse of 5 minutes, 10 minutes and 30 minutes was confirmed:

Sterilization target: *Citrus unshiu*
Quasi-contamination: spore of *Penicillium digitatum*
Power source: 10 kVpp, 9-11 kHz (LHV-10AC manufactured by Logy Denshi Co. Ltd.
Width of Sheet-shaped electrodes: 3 mm, 5 mm Temporal sterilization results obtained by using each of the sheet-shaped electrodes having the width of 3 mm and the width of 5 mm are shown in photographs of FIGS. 13(*b*) and (*c*), respectively. It was confirmed from the obtained results that the sterilization was gradually conducted after a lapse of 5 seconds, an almost full sterilization was conducted after a lapse of 30 minutes, and the sterilization effects depended on the irradiation period of time. It became clear that the sterilization range per a single sheet-shaped electrode widely expanded circumferentially, without staying directly below the sheet-shaped electrode, and the sterilization could be conducted with a wider range than the actual width of the sheet-shaped electrode. It was confirmed that the range of capacity of the sterilization per a single sheet-shaped electrode widely expanded circumferentially, without staying directly below the sheet-shaped electrode, in this manner, and the sterilization could be conducted with a wider range than the actual width of the sheet-shaped electrode, thus providing an expanded area of discharge to conduct an effective sterilization processing.

DESCRIPTION OF REFERENCE NUMERALS 1 voltage-applying unit
2 pair of electrode
2*a* one electrode
2*b* another electrode
21 dielectric
22 conductor
22*a* second conductor
23 contact piece
23*a* movable conductor
3 position changing unit
4 measurement unit
5 control unit
100 sterilization target

What is claimed is:

1. A plasma sterilization apparatus configured to apply a voltage to an agricultural product as a sterilization target having conductivity comprising:
   a power source;
   multiple pairs of electrodes, each electrode having the same shape respectively, that apply, between one electrode and another electrode of each pair, in a discharged state, said voltage, supplied from said power source, to said sterilization target via a dielectric and wherein each of the electrodes is flexible and comprises a conductor covered with said dielectric; and
   a position changing unit configured to change a relative position between said pairs of electrodes and said sterilization target.

2. The plasma sterilization apparatus as claimed in claim 1, wherein:
   said dielectric is formed of fiber, synthetic resin or silicone resin having a fiber form or a mesh form.

3. The plasma sterilization apparatus as claimed in claim 1, wherein:
   said position changing unit moves said sterilization target relative to said pairs of electrodes.

4. The plasma sterilization apparatus as claimed in claim 1, wherein:
   said position changing unit rotates each of said electrodes, to bring at least a front portion of at least one of said electrodes into contact with said sterilization target.

5. The plasma sterilization apparatus as claimed in claim 1,
   wherein the plasma sterilization apparatus is further configured to measure an impedance value of said sterilization target and
   to control a change in said relative position provided by said position changing unit, based on the measured impedance value.

6. The plasma sterilization apparatus as claimed in claim 1, wherein: said voltage can be changed in response to a kind of said sterilization target.

7. A plasma sterilization apparatus configured to apply a voltage to a sterilization target having conductivity comprising:
   a power supply;
   a pair of electrodes that apply, between one electrode and another electrode of the pair, in a discharged state, the voltage, supplied from said power source, to said sterilization target via a dielectric and wherein each of the electrodes comprises plural pairs of flexible contact pieces and a conductor covered with said dielectric;
   a conveyor configured to change a relative position between said pair of electrodes and said sterilization target;
   wherein the plasma sterilization apparatus is further configured to measure an impedance value of said sterilization target and to control a change in said relative position provided by said position changing unit, based on the measured impedance value.

\* \* \* \* \*